United States Patent
Schaffer

(10) Patent No.: US 9,696,263 B2
(45) Date of Patent: Jul. 4, 2017

(54) BORESCOPE CALIBRATOR AND USER CHECK GAUGE

(71) Applicant: THE BOEING COMPANY, Chicago, IL (US)

(72) Inventor: Michael J. Schaffer, Olympia, WA (US)

(73) Assignee: THE BOEING COMPANY, Chicago, IL (US)

( * ) Notice: Subject to any disclaimer, the term of this patent is extended or adjusted under 35 U.S.C. 154(b) by 88 days.

(21) Appl. No.: 14/930,069

(22) Filed: Nov. 2, 2015

(65) Prior Publication Data

US 2017/0122879 A1    May 4, 2017

(51) Int. Cl.
*G01J 1/10*   (2006.01)
*G01N 21/93*  (2006.01)
*G01N 21/88*  (2006.01)

(52) U.S. Cl.
CPC ......... *G01N 21/93* (2013.01); *G01N 21/8803* (2013.01); *G01N 2201/13* (2013.01)

(58) Field of Classification Search
CPC ........... G01N 2201/13; G01N 21/8803; G01N 21/93; G01N 21/9515; G01N 21/954; H01J 29/45; H01J 9/233; H04N 13/0025; H04N 13/0221; H04N 13/0431
USPC ............................................ 356/243.1–256
See application file for complete search history.

(56) References Cited

U.S. PATENT DOCUMENTS 7,312,454 B2   12/2007   Safai et al.
8,350,894 B2    1/2013   Turner et al.

*Primary Examiner* — Tri T Ton
(74) *Attorney, Agent, or Firm* — Patterson + Sheridan, LLP

(57) ABSTRACT

A borescope calibration device is provided that includes a base having a planar surface and a plurality of reference surfaces on a side of the base opposing the planar surface, each of the plurality of reference surfaces having a height that decreases along a length of the base, a fixture that positions an optical head along a reference line that is parallel to the planar surface and providing a fixed distance between the reference surfaces and the optical head, the fixture being movable along a length of the base, and a target pattern formed on each of the reference surfaces.

20 Claims, 3 Drawing Sheets

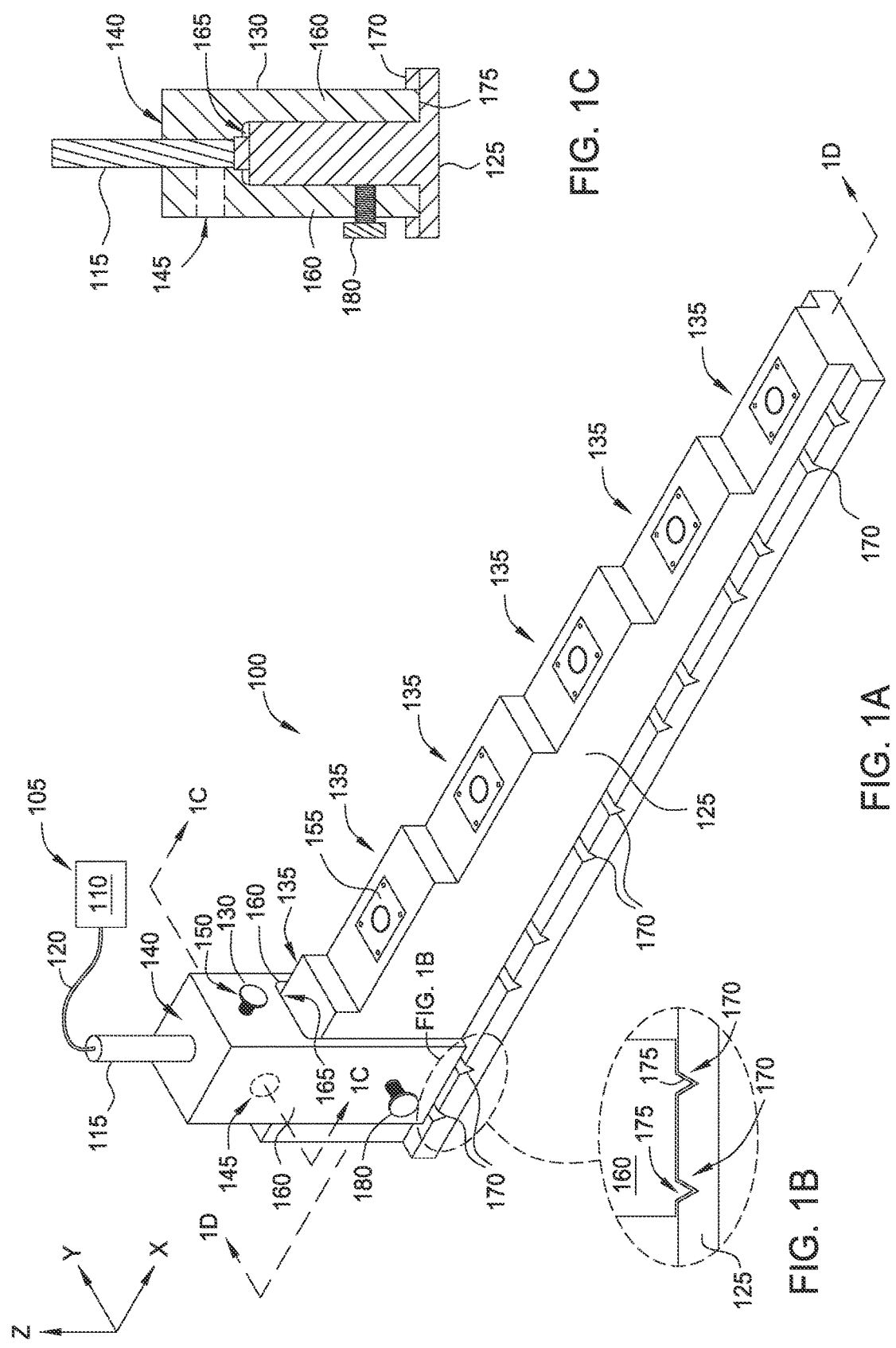

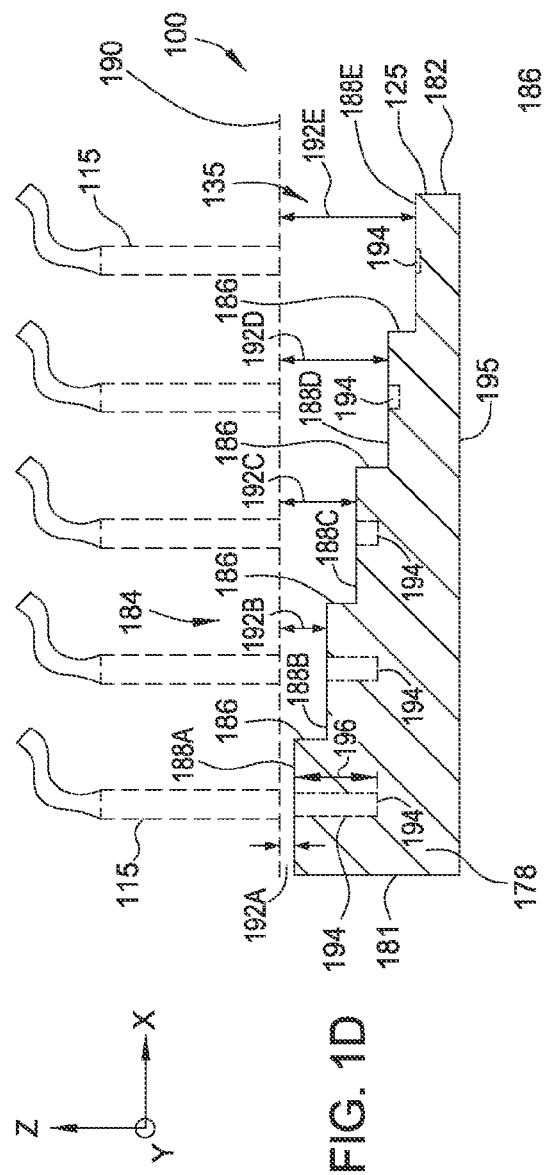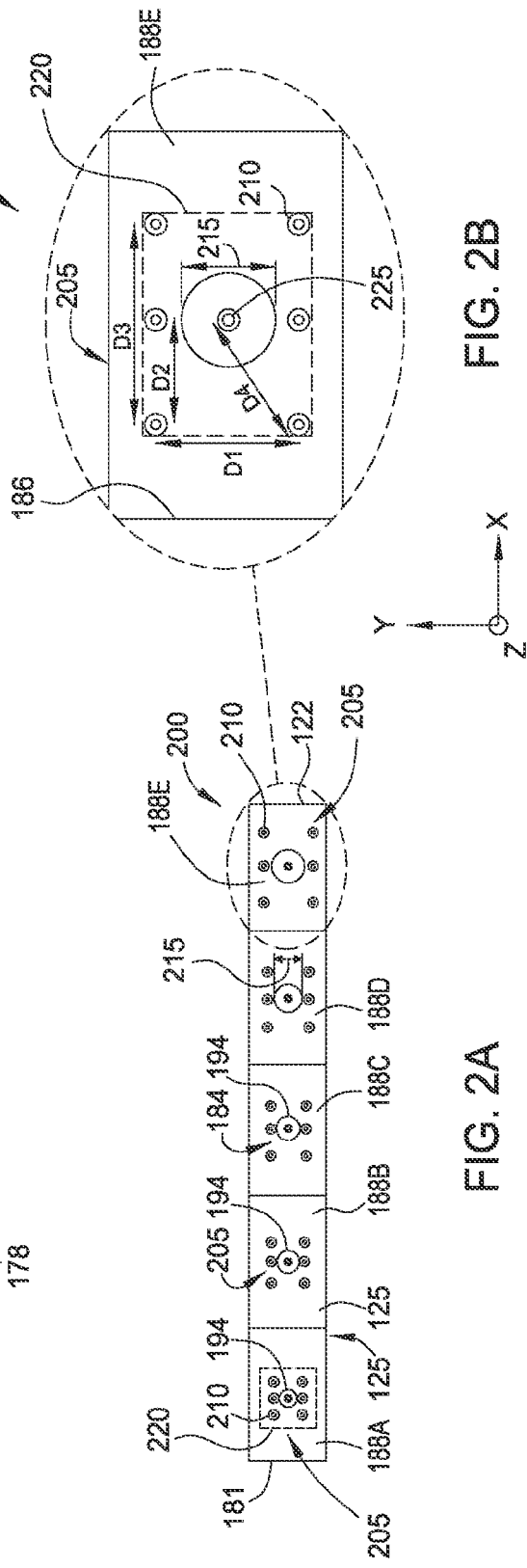

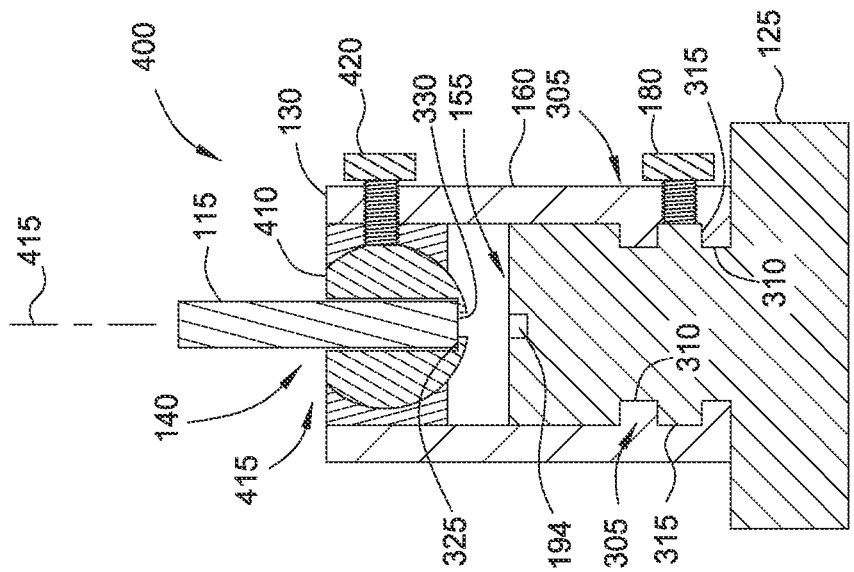
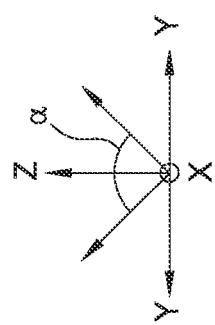
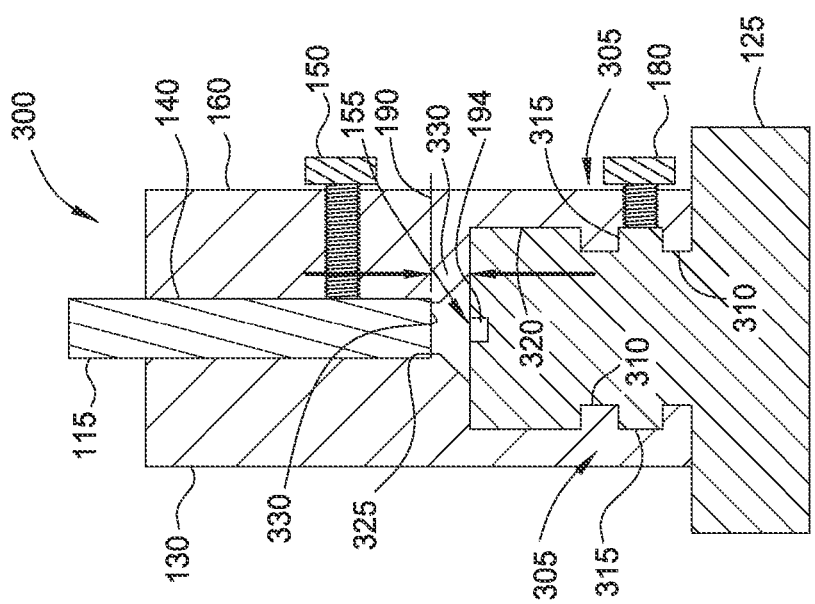
FIG. 3
FIG. 4

BORESCOPE CALIBRATOR AND USER CHECK GAUGE

BACKGROUND

Description of the Related Art

Borescopes are used for visual inspection in an area that may be inaccessible by other means, and can be utilized as a nondestructive testing device for recognizing defects or imperfections in a structure or substructure. Borescopes can be used in the visual inspection of aircraft engines, industrial gas turbines, steam turbines, generators, and automotive and truck engines, for safety and maintenance requirements. Borescope inspection can be used to prevent unnecessary maintenance or determine necessary maintenance due to the presence of a defect. Borescopes can also be used to inspect critical interior surfaces for imperfections in machined or cast parts, such as burrs or cracks. Borescopes may also be utilized to verify surface finish of parts. Similar optical instruments utilized in the medical field are endoscopic devices commonly referred to as endoscopes.

Borescopes require calibration and are initially calibrated by the manufacturer, but typically do not include a certification of the accuracy of measurement. The lack of certification may be due to the absence of an adequate calibration standard that could be duplicated and utilized throughout the world. However, in many industries, accuracy of measurement and/or a measurement uncertainty of the borescope is required.

Therefore, there exists a need for a calibration device or gauge that may be used by personnel in the field to determine the accuracy of measurement of a borescope.

SUMMARY

Aspects disclosed herein relate to methods of calibrating a borescope and a portable gauge device for calibration of a borescope by a user on-site or in the field.

In one example, a borescope calibration device is provided that includes a base having a planar surface and a plurality of reference surfaces on a side of the base opposing the planar surface, each of the plurality of reference surfaces having a height that decreases along a length of the base, a fixture that positions an optical head along a reference line that is parallel to the planar surface and providing a fixed distance between the reference surfaces and the optical head, the fixture being movable along a length of the base, and a target pattern formed on each of the reference surfaces.

In another example, a borescope calibration device is provided that includes a base having a planar surface and a plurality of reference surfaces on a side of the base opposing the planar surface, a fixture that is movable relative to the base and positions an optical head along a reference line that is parallel to the planar surface and providing a fixed distance between the reference surfaces and the optical head, the fixed distance increasing from a first end of the base to a second end of the base, and a target pattern formed on each of the reference surfaces, wherein each of the target patterns comprise two or more points that are laterally spaced at a known distance and a blind hole provided at a known depth from the reference surface.

In another example, a borescope calibration device is provided that includes a base having a planar surface and a stepped surface on a side of the base opposing the planar surface, the stepped surface having a plurality of reference surfaces, a fixture that positions an optical head along a reference line that is parallel to the planar surface and maintains a fixed distance between the reference surfaces and the optical head, the fixture being movable along a length of the base, and a target pattern formed on each of the reference surfaces, wherein each of the target patterns comprise two or more points that are laterally spaced at a known distance.

BRIEF DESCRIPTION OF THE DRAWINGS

Having generally described the various examples of the disclosure, reference will now be made to the accompanying drawings.

FIG. 1A is an isometric view of one example of a calibration tool.

FIG. 1B is an enlarged partial side view of the calibration tool of FIG. 1A.

FIG. 1C is a cross-sectional view of the calibration tool of FIG. 1A along lines 1C-1C.

FIG. 1D is a cross-sectional view of the base of FIG. 1A along lines 1D-1D.

FIG. 2A is a plan view of a reference surface of the calibration tool of FIGS. 1A-1D.

FIG. 2B is an enlarged plan view of a reference surface of the calibration tool of FIG. 2A.

FIG. 3 is a side cross-sectional view of another example of a calibration tool.

FIG. 4 is a side cross-sectional view of another example of a calibration tool.

To facilitate understanding, identical reference numerals have been used, where possible, to designate identical elements that are common to the figures. It is contemplated that elements disclosed in one example may be beneficially utilized in other examples without specific recitation.

DETAILED DESCRIPTION

Aspects disclosed herein relate to calibration of a borescope and a portable gauge device for calibration of the borescope by a user on-site or in the field. The device may be utilized at any time or place by personnel in the field to ensure measurement accuracy of a borescope. The device may be utilized to save time by streamlining an on-site inspection process.

FIGS. 1A-1D are various views of one example of a calibration tool 100 that may be used to calibrate, and/or as a check gauge for, a borescope 105. FIG. 1A is an isometric view of the calibration tool 100, FIG. 1B is an enlarged partial side view of the calibration tool 100 of FIG. 1A, FIG. 1C is a cross-sectional view of the calibration tool 100 of FIG. 1A along lines 1C-1C, and FIG. 1D is a cross-sectional view of the base 125 of FIG. 1A along lines 1D-1D.

The borescope 105 includes a monitor 110 that receives a signal from an optical head 115 via an optical transmission member 120. The optical head 115 may include lighting devices and a camera (both not shown) that provide a visual signal and/or a measurement metric to the monitor 110. The optical transmission member 120 may be rigid or flexible. The optical head 115 is inserted into small spaces, openings or volumes in order to facilitate measurement and/or inspection of objects or surfaces that may not otherwise be visible without the use of the borescope 105.

The calibration tool 100 includes a base 125 and a fixture 130. The fixture 130 is selectively movable relative to the base 125 such that the fixture 130 may be moved adjacent to multiple measurement areas 135 disposed along a length of the base 125. The fixture 130 may include at least one opening shown as opening 140 and an optional opening 145 (shown in dashed lines) where the optical head 115 may be at least partially received. The opening 140 may be used when the optical head 115 includes a direction of view (DOV) of 0 degrees, and the optional opening 145 may be used when the optical head 115 has an angular DOV (such as 45 degrees or 90 degrees) relative to an X-Y plane. When the opening 140 (or the optional opening 145) is used, a set screw 150 may be disposed on the fixture 130 in order to secure the optical head 115 within the opening 140 (or the optional opening 145).

The fixture 130 is slidably disposed on the base 125 in the X direction such that the optical head 115 may be positioned to view any number of the measurement areas 135. Each of the measurement areas 135 includes a target pattern 155 that may be used to evaluate and/or calibrate the borescope 105. The fixture 130 may include an opening 165 through side 160 to receive the base 125. A width of the opening 165 may be slightly greater than a width of the base 125 such that a tight tolerance is provided therebetween. Thus, the fixture 130 may move in the X direction along the base 125 without rotation about a vertical axis (Z axis or in the X-Y plane) or tilting in the Y-Z plane.

In one example, one or both of the base 125 and the fixture 130 may include indexing features 170. The indexing features 170 may be utilized to center or align the fixture 130 (and the optical head 115) relative to the target pattern 155. The indexing features 170 may be grooves, channels or bumps that interact with a mating indexing feature 175 on the fixture 130. The indexing features 170 may provide a physical stop and/or a tactile sensation indicating to a user the proper positioning of the fixture 130 relative to the base 125.

When the proper position of the fixture 130 is determined, with or without utilization of the indexing feature 170, the optical head 115 may be located at a known position relative to the target pattern 155, and a set screw 180 may be utilized to fix the fixture 130 to the base 125. Alternatively, or in combination, the set screw 180 may not be used such that the fixture 130 may be moved in the X direction relative to laterally spaced points of the target pattern 155.

The base 125 and the fixture 130 may be made from a rigid material, such as a metallic material, to resist bending, deflection and/or expansion and contraction. The set screws 150 and 180 may be metallic or a plastic material and may be configured to rotate by hand, such as thumb-screws. A size of the calibration tool 100 may vary but is generally sized to be hand-held and highly portable. In one example, a length of the base may be about 5 inches to about 7 inches, or greater, and the calibration tool 100 may weigh about 2 pounds to about 6 pounds when made of a metallic material, such as steel.

FIG. 1D is a cross-sectional view of the base 125 of FIG. 1A along lines 1D-1D. The fixture 130 is not shown in this view and multiple optical heads 115 are shown in phantom above the base 125 in order to show one example of operation of the calibration tool 100. In practice, a single borescope, having the optical head 115 coupled thereto, will be calibrated using the calibration tool 100. Calibration may be provided by positioning the optical head 115 at each of the measurement areas 135.

In one example, the base 125 includes a body 178 having a first end 181 and a second end 182. A stepped surface 184, which includes the measurement areas 135, is provided along the length of the body 178. The stepped surface 184 includes a plurality of steps 186 that reduce a height dimension (in the Z direction) of the body 178 from the first end 181 to the second end 182. Each of the measurement areas 135 along the stepped surface 184 include a reference surface, indicated as surfaces 188A-188E, having the target pattern 155 (shown in FIG. 1A). At each position along the stepped surface 184, the optical head 115 is positioned along reference line 190. Reference line 190 is provided by mounting the optical head 115 in the fixture 130 (shown in FIGS. 1A and 1C). Reference line 190 may be located at the viewing end of the optical head 115 when the optical head 115 is positioned in the fixture 130. Reference line 190 is generally parallel to each of the reference surfaces 188A-188E along the X direction. However, a distance between the reference line 190 and the reference surfaces 188A-188E increases from the first end 181 to the second end 182 of the body 178. The reference line 190 may also be parallel to a planar surface 195 of the base 125 that opposes the reference surfaces 188A-188E. The reference surfaces 188A-188E may be disposed in respective X-Y planes that are parallel to an X-Y plane of the planar surface 195 of the base 125. The positioning of the optical head 115 along the reference line 190 is maintained by the fixture 130 as the fixture 130 moves along the base 125 in the X direction.

At the first end 181, the reference surface 188A includes a first stand-off distance 192A between the reference surface 188A and the reference line 190. A second stand-off distance 192B, a third stand-off distance 192C, a fourth stand-off distance 192D and a fifth stand-off distance 192E gradually increases along the X direction from the first end 181 to the second end 182 of the body 178. The stand-off distances 192A-192E may be based on a depth of field (DOF) and/or a field of view (FOV) for a specific borescope. The first stand-off distance 192A may be a near FOV and the fifth stand-off distance 192E may be a far FOV for a particular borescope. In one example, the first stand-off distance 192A may be about 5 millimeters (mm), the second stand-off distance 192B may be about 10 mm, the third stand-off distance 192C may be about 15 mm, the fourth stand-off distance 192D may be about 20 mm and the fifth stand-off distance 192E may be about 25 mm for a particular borescope. The stand-off distances 192A-192E may be different for a borescope having a different FOV and/or DOF.

In addition the target pattern 155 includes an opening, such as blind holes 194. The blind holes 194 may be provided in each of the reference surfaces 188A-188E. The blind holes 194 may be formed to a known depth in each of the reference surfaces 188A-188E and have a known distance from the reference line 190. Sizes of the blind holes 194 may vary along the stepped surface 184. The sizes of the blind holes 194 may also vary based on the FOV and/or DOF of a particular borescope. In the example shown in FIG. 1D, a depth 196 of the blind hole 194 from the reference surface 188A may be about 19 mm, and depths of the blind holes 194 from the remaining reference surfaces 188B-188E may decrease along the body 178 from the first end 181 to the second end 182. In one example, a depth of each of the blind holes 194 may decrease (along the X direction from the reference surface 188A to the second end 182 of the body 178) by about 3 mm to about 5 mm from the reference surfaces 188B-188E. The depth of each of the blind holes 194 is known and is traceable to NIST standards. As the optical head 115 is moved to positions facing the reference surfaces 188A-188E, measurements of the stand-off distances 192A-192E, as well as depths of the blind holes 194 may be performed, and the results are recorded.

FIG. 2A is a plan view of a reference surface of the calibration tool of FIGS. 1A-1D. The calibration tool 200 includes a base 125 having reference surfaces 188A-188E along a stepped surface 184 and a fixture 130 (not shown). The base 125 shown in FIG. 2A may be used with the fixture 130 of the calibration tool 100 shown in FIG. 1A.

Each of the reference surfaces 188A-188E includes a target pattern 205 which include a plurality of planner points 210 and a blind hole 194. Each of the planner points 210 may be a physical mark, such as a depression or groove, or may be a paper or plastic decal. Alternatively, the planner points 210 may be a reticle made of a transparent material, such as glass or quartz. In some examples, each of the blind holes 194, at a geometric center thereof, may include a planner point as described herein.

A diameter of 215 of the blind holes 194 (shown at reference surface 188D) in each of the reference surfaces 188A-188E may increase from the first end 181 to the second end 182 of the body 178. The increase in the diameter 215 of the blind holes 194 from the first end 181 to the second end 182 of the body 178 may correspond to the increase in the stand-off distances 192A-192E (shown in FIG. 1D) from the first end 181 to the second end 182 of the body 178. In addition, a surface area 220 of the target patterns 205 (shown at reference surface 188A) may increase from the first end 181 to the second end 182 of the body 178.

FIG. 2B is an enlarged plan view of the reference surface 188E of the calibration tool 200 of FIG. 2A. In one example, the target pattern 205 formed on or in the reference surface 188E has the largest surface area 220 and the blind hole 194 may have the largest diameter 215 of the calibration tool 200. However, as described in FIG. 1D, the depth of the blind hole 194 may be less than depths of the other blind holes 194. In one example, the blind hole 194 includes a planner point 225 which is similar to the planner points 210. Distances between the planner points 210 and 225, exemplarily shown as D1-D4, are known. Lateral measurements (e.g., in the X or Y directions) as well as diagonal measurements (in the X-Y plane) may be taken between two or more of the planner points 210, 225, and the results are recorded.

The distances between the planner points 210 and 225 and depths of the blind holes 194 from the reference surfaces 188A-188E are known and are traceable to National Institute of Standards and Technology (NIST) standards. "Traceable" as used herein can be defined as an unbroken record of documentation (e.g., "documentation traceability") or an unbroken chain of measurements and associated measurement uncertainties (e.g., "metrological traceability").

FIG. 3 is a side cross-sectional view of another example of a calibration tool 300. In this example, a slide interface 305 is provided between the base 125 and the fixture 130. The slide interface 305 may include one or more grooves 310 that interface with one or more channels 315 formed between the base 125 and the fixture 130. The grooves 310 may run along a length of the base 125 (in the X direction). Likewise, the channels 315 may be formed in an interior surface 320 of the sides 160 of the fixture 130 along a length of the fixture 130 (in the X direction). In some examples, the set screw 180 may seat on a surface of the base 125 adjacent to a channel 315.

Also shown in this example is a reference seat 325 where an end 330 of the optical head 115 may be positioned. The reference seat 325 may be a continuous or intermittent ring or shoulder formed at an end of the opening 140 adjacent to the target pattern 155. Positioning the optical head 115 within the opening 140 to stop at the reference seat 325, and tightening the set screw 150, positions the optical head 115 at the reference line 190 and provides a known stand-off distance 332 (similar to the stand-off distances 192A-192E (shown in FIG. 1D)).

FIG. 4 is a side cross-sectional view of another example of a calibration tool 400. The calibration tool 400 is substantially similar to the calibration tool 300 shown in FIG. 3 with the following exception. In this example, the fixture 130 includes a pivoting device 405 that receives the optical head 115. The pivoting device 405 may be a gimbal device having a spherical member 410 providing movement of the optical head 115 relative to the target pattern 155. The pivoting device 405 may be utilized to adjust an incident angle and/or a viewing angle of the optical head 115 relative to the target pattern 155. The pivoting device 405 may be utilized to tilt the optical head 115 relative to a normal line of sight 415 of the optical head 115. For example, the pivoting device 405 may be utilized to tilt the optical head 115 in the Y-Z plane or the X-Z plane. The pivoting device 405 may be utilized to tilt the optical head 115 along an angle α in the Y-Z plane (shown in the inset in FIG. 4). The angle α may be between 0 degrees (e.g., in the Z direction (same as the normal line of sight 415)) to about 45 degrees relative to the normal line of sight 415 of the optical head 115. While not shown in this view, the optical head 115 may be movable in the angle α in the X-Z plane.

If desired, the optical head 115 may be secured using a set screw 420 that may be rotated against an outer surface of the spherical member 410. While not shown in this view, the set screw 150 may be aligned along the X direction to secure the optical head 115 within the fixture 130, similar to the example shown in FIG. 1A. The set screw 420 may be used when the optical head 115 is moved to a desired angle within the angle α. The optical head 115 may be fixed at a desired angle and the fixture 130 may be moved relative to the base 125 (specifically the target pattern 155) in order to measure distances between planner points 210 (shown in FIG. 2A). Alternatively, the fixture 130 may be fixed to the base 125 and the optical head 115 may be moved along the angle α in order to measure distances between planner points 210.

Examples of the calibration tools 100, 200, 300, and 400 as described herein provides a portable gauge device for calibration of the borescope by a user on-site or in the field. The calibration tools 100, 200, 300, and 400 as described herein may be utilized at any time or place by personnel in the field to ensure measurement accuracy of a borescope. The target surfaces of the calibration tools 100, 200, 300, and 400 as described herein include both depth and plan view calibration marks that are traceable to NIST standards. The calibration tools 100, 200, 300, and 400 as described herein provide measurement in three dimensions (left to right, front to back and depth) which is an improvement over conventional calibration devices which typically are only capable of providing one dimensional measurement. The calibration tools 100, 200, 300, and 400 as described herein may also be used for calibration in laboratory environments.

While the foregoing is directed to examples of the present disclosure, other and further examples of the disclosure thus may be devised without departing from the basic scope thereof, and the scope thereof is determined by the claims that follow.

The invention claimed is:

1. A borescope calibration device, comprising:
    a base having a planar surface and a plurality of reference surfaces on a side of the base opposing the planar surface, each of the plurality of reference surfaces having a height that decreases along a length of the base;

a fixture that positions an optical head along a reference line that is parallel to the planar surface and providing a fixed distance between the reference surfaces and the optical head, the fixture being movable along a length of the base; and a target pattern formed on each of the reference surfaces.

2. The calibration device of claim 1, wherein each of the target patterns comprise two or more points that are laterally spaced at a known distance.

3. The calibration device of claim 2, wherein the known distance on each target pattern increases from a first end of the base to a second end of the base.

4. The calibration device of claim 2, wherein each of the target patterns include a blind hole provided at a depth from a respective reference surface.

5. The calibration device of claim 4, wherein the depth of each of the blind holes decreases from a first end of the base to a second end of the base.

6. The calibration device of claim 4, wherein each of the blind holes includes a diameter that increases from a first end of the base to a second end of the base.

7. The calibration device of claim 1, wherein the optical head is disposed in an opening formed in the fixture at an angle of 0 degrees relative to the reference surfaces.

8. The calibration device of claim 1, wherein the optical head is disposed in an opening formed in the fixture at an angle between about 10 degrees to about 90 degrees relative to the reference surfaces.

9. The calibration device of claim 1, wherein the fixture includes a pivoting device having an opening for receiving the optical head, the pivoting device being positionable to vary a viewing angle of the optical head relative to a respective reference surface.

10. The calibration device of claim 1, wherein the fixed distance increases from a first end of the base to a second end of the base.

11. A borescope calibration device, comprising:
a base having a planar surface and a stepped surface on a side of the base opposing the planar surface, the stepped surface having a plurality of reference surfaces;
a fixture that positions an optical head along a reference line that is parallel to the planar surface and maintains a fixed distance between the reference surfaces and the optical head, the fixture being movable along a length of the base; and
a target pattern formed on each of the reference surfaces, wherein the each of the target patterns comprise two or more points that are laterally spaced at a known distance.

12. The calibration device of claim 11, wherein the known distance on each target pattern increases from a first end of the base to a second end of the base.

13. The calibration device of claim 11, wherein each of the target patterns include a blind hole provided at a depth from the reference surface.

14. The calibration device of claim 13, wherein the depth of each of the blind holes decreases from a first end of the base to a second end of the base.

15. The calibration device of claim 13, wherein each of the blind holes includes a diameter that increases from a first end of the base to a second end of the base.

16. A borescope calibration device, comprising:
a base having a planar surface and a plurality of reference surfaces on a side of the base opposing the planar surface;
a fixture that is movable relative to the base and positions an optical head along a reference line that is parallel to the planar surface and providing a fixed distance between the reference surfaces and the optical head, the fixed distance increasing from a first end of the base to a second end of the base; and
a target pattern formed on each of the reference surfaces, wherein the each of the target patterns comprise two or more points that are laterally spaced at a known distance and a blind hole provided at a known depth from a respective reference surface.

17. The calibration device of claim 16, wherein the known distance on each target pattern increases from the first end of the base to the second end of the base.

18. The calibration device of claim 16, wherein a depth of each of the blind holes decreases from the first end of the base to the second end of the base.

19. The calibration device of claim 16, wherein each of the blind holes includes a diameter that increases from the first end of the base to the second end of the base.

20. The calibration device of claim 16, wherein the fixture includes a pivoting device having an opening for receiving the optical head, the pivoting device being positionable to vary a viewing angle of the optical head relative to a respective reference surface.

* * * * *